United States Patent [19]
Tsuei et al.

[11] Patent Number: 5,589,194
[45] Date of Patent: Dec. 31, 1996

[54] METHOD OF ENCAPSULATION AND MICROCAPSULES PRODUCED THEREBY

[75] Inventors: Alexander C. Tsuei, Woodbury; Lorenz Kogl, III, Stillwater; Daniel B. Pendergrass, Jr., Mendota Heights, all of Minn.

[73] Assignee: Minnesota Mining and Manufacturing Company, St. Paul, Minn.

[21] Appl. No.: 123,806

[22] Filed: Sep. 20, 1993

[51] Int. Cl.$^6$ ............. A61K 9/50; A23L 1/236; A23P 1/04; B01J 13/04

[52] U.S. Cl. ............. 424/497; 51/304; 252/301.65; 252/357; 264/4.4; 424/498; 426/99; 426/516; 426/548; 427/213.3; 427/213.31; 427/213.36; 428/321.5; 428/402.2; 428/402.22; 428/402.24; 502/527; 514/963; 514/965

[58] Field of Search .............. 264/4.4; 427/213.3, 427/213.31, 213.36; 428/402.2, 402.22, 321.5, 402.24; 514/963, 965; 424/498, 401, 497; 8/521; 502/527; 411/258; 156/305, 314; 426/99, 516

[56] References Cited

U.S. PATENT DOCUMENTS

| | | | |
|---|---|---|---|
| 2,907,682 | 10/1959 | Eichel | 428/321.5 X |
| 3,161,602 | 12/1964 | Herbig et al. | 427/213.36 |
| 3,242,237 | 3/1966 | Belak et al. | 264/13 |
| 3,389,194 | 6/1968 | Somerville | 264/4 |
| 3,423,489 | 1/1969 | Arens et al. | 264/4 |
| 3,779,942 | 12/1973 | Bolles | 428/402.2 |
| 3,856,699 | 12/1974 | Miyano et al. | 427/213.3 |
| 4,102,806 | 7/1978 | Kondo et al. | 427/213.3 |
| 4,112,631 | 9/1978 | Howard | 51/295 |
| 4,211,668 | 7/1980 | Tate | 264/4.3 |
| 4,519,961 | 5/1985 | Schumacher et al. | 264/4.6 |
| 4,597,970 | 7/1986 | Sharma et al. | 426/5 |
| 4,698,264 | 10/1987 | Steinke | 428/402.2 |
| 4,800,087 | 1/1989 | Mehta | 424/497 |
| 4,828,857 | 5/1989 | Sharma et al. | 426/285 |
| 4,842,863 | 6/1989 | Nishimura et al. | 424/498 X |
| 5,200,236 | 4/1993 | Lang et al. | 427/213 |
| 5,204,029 | 4/1993 | Morgan et al. | 264/4.4 |
| 5,270,055 | 12/1993 | Moest | 424/498 X |

FOREIGN PATENT DOCUMENTS

| | | |
|---|---|---|
| 0443743 | 5/1991 | European Pat. Off. . |
| 2336176 | 1/1975 | France . |
| WO8807816 | 10/1988 | WIPO . |

OTHER PUBLICATIONS

Kirk–Othmer *Encyclopedia of Chemical Technology*; 3d, vol. 1 pp. 1–9 (1978).

*Primary Examiner*—Richard D. Lovering
*Attorney, Agent, or Firm*—Gary L. Griswold; Walter N. Kirn; Dale A. Bjorkman

[57] ABSTRACT

Microcapsules are prepared by dispersing or dissolving an active component or components in a solid matrix-forming material that has been thermally softened to form an encapsulation composition. The encapsulation composition is injected as an intact stream into a quenching liquid to provide solid microcapsules.

17 Claims, 4 Drawing Sheets

METHOD OF ENCAPSULATION AND MICROCAPSULES PRODUCED THEREBY

FIELD OF THE INVENTION

The present invention relates to a microencapsulation method. More particularly the present invention relates to a process to encapsulate discrete particulate, multiparticulate and liquid multicore materials or to produce microcapsules containing homogeneous dissolved ingredients.

BACKGROUND

Encapsulation is a well-known technique in the art for protecting components that are sensitive to the elements or for providing time-released delivery of active ingredients. Certain ingredients are easy to encapsulate using conventional techniques. Others, such as sensitive water-soluble components like Vitamin C or aspartamine, are very difficult to encapsulate so that controlled protection and release is provided.

E.P. 0 443 743 to Kubota discloses a method to encapsulate particulate Vitamin C in fine lipid powders by bringing a particulate core substance containing Vitamin C into contact collidingly with particles of a coating material composed of one or more fine powdery lipids, so as to form a coating layer of agglomerated particles of the coating material surrounding the entire particulate core substance.

U.S. Pat. No. 3,161,602 to Herbig discloses a process for making capsules utilizing a three-phase system: a wax-like wall material, a nucleus material, and a substantially inert oily vehicle. The system is heated so that the waxy material melts to a liquid, and is agitated so that the liquid waxy material deposits on each entity of the nucleus material, thereby forming liquid-walled capsule precursor droplets. The entire solution is then cooled with continued agitation, solidifying the waxy walls and forming self-sustaining capsules. This capsule making process has an undesirably long time span from the formation of liquid droplets to the completely solid capsules, which may cause loss of the active component either via diffusion or exclusion mechanisms into the hot inert oily vehicle. This process needs high mechanical agitation and may produce capsules having an uneven distribution of active ingredient in the capsules. This process also produces capsules having a very broad size distribution.

U.S. Pat. Nos. 4,597,970 and 4,828,857, to Sharma, et. al. describe a method to encapsulate aspartame in hydrogenated palm oil by a spray drying process. The process has disadvantages shared with other air spray processes in that it is difficult to provide a uniform, continuous layer onto the outermost surface of the droplets during the congealing step.

U.S. Pat. No. 3,423,489, to Arens, et.al and U.S. Pat. No. 3,779,942, to Bolles disclose a method of forming capsules by forming concentric biliquid columns having an inner core of liquid to be encapsulated and an outer tube of hardenable liquid encapsulating material. The column is caused to travel in a trajectory path for a time sufficient to allow the column to constrict into individual droplets in which the encapsulating material encloses the encapsulated liquid. The stream is preferably directed to travel through a gaseous phase rather than a liquid medium, Column 2, lines 47–51. This method requires the use of special multiple orifice liquid discharging equipment.

U.S. Pat. No. 3,242,237, to Belak, et. al. discloses a process for forming discrete slow release fertilizer particles. According to this method, solid fertilizer is dispersed in melted wax and dropped into water in the form of droplets. Upon contact with the water, the droplets immediately solidify in particle form, and can be separated from the water.

U.S. Pat. No. 3,389,194 to Somerville discloses a method for mass producing small spherical particles. In this process, concentric rods of a fluid fill material and a separate shell or film material are extruded into a conduit through which a stream of carrier fluid is swept. Because the carrier fluid passes the concentric rods of fluid fill material and shell material at a faster rate of flow than the rate of extrusion, the rods are caused to elongate and break off into individual segments. The shell material hardens by cooling or by chemical reaction or solvent extraction.

SUMMARY OF THE INVENTION

This invention relates to a method of encapsulation and microcapsules obtained therefrom. For purposes of the present invention, the article produced by the process described herein will be called "microcapsules" and is intended to contemplate encapsulated discrete particulate, multiparticulate, liquid multicore and homogeneously dissolved active components. The microcapsules of the present invention may be spherical, symmetrical or of irregular shape. In carrying out the encapsulation method, an encapsulation composition is formed by first dispersing or dissolving at least one active component to be encapsulated in a solid matrix-forming material that has been thermally softened. The encapsulation composition is then injected as an intact stream into a quenching liquid, where the composition breaks up into discrete droplets that are then quenched to provide solid particles containing the active agent. The quenching liquid is selected to be substantially non-reactive with the active component and the solid matrix-forming material, and to be a poor solvent for the solid matrix-forming material. Preferably, the quenching liquid is a poor solvent for both the active component and the solid matrix-forming material. For purposes of the present invention, a material is considered to chemically non-reactive or a poor solvent for another material if a reaction or solvation does not occur to a significant degree on the time scale of the droplet formation, solidification and collection processes. Perfluorocarbons are particularly suited for use as the quenching liquid.

DETAILED DESCRIPTION OF THE INVENTION

This encapsulation method may provide either a water soluble or oil soluble active component encapsulated in a shell matrix of either a water or oil soluble material. The microencapsulated active component may be protected from oxidation and hydration, and may be released by melting, rupturing, biodegrading, or dissolving the surrounded shell matrix or by slow diffusion of the active component through the matrix.

The present invention comprises a number of particular aspects of benefit as compared to prior encapsulation methods. Specifically, the present invention utilizes raw materials that are readily reusable and may have comparatively low volatility. Thus, the present invention does not introduce harmful volatile components into the atmosphere and can exhibit much less adverse pollution effects on the environment. Additionally, because the quenching liquid is preferably an inert fluid it is relatively easy to recycle and remove active components therefrom so that the same liquid may be reused again and again. The present encapsulation technique takes place under moderate conditions, so that there need be no acidic media to dispose of and no use or generation of noxious components such as formaldehyde and the like. Thus, as compared to conventional encapsulation techniques such as polyoxymethylene urea encapsulation processes, the present process is relatively "environment friendly."

The present encapsulation technique has a distinct advantage over other coating techniques such as spray-drying, because it may provide uniform size distribution and uniform shapes of microcapsules. Prior processes, such as spray drying, require substantial separation and sorting of microcapsules to achieve the same uniformity of size and shape.

The present process advantageously can be controlled to provide a high percentage of microcapsules comprising both matrix and active component, as opposed to formation of microcapsules having no active component, which microcapsules are waste or "trash." The amount of active component to be incorporated in microcapsules may be readily and closely controlled by adjustment to the concentration in the encapsulation composition before injection of the stream. The size of the microcapsule may be readily controlled by proper balance of pressure, temperature and viscosity of the encapsulation composition and quenching liquid. The shape of the microcapsule also can be controlled by adjustment of these parameters. For example, by adjusting the temperature of the quenching liquid to be at the high range of the appropriate working temperature of the system, clustered or flattened microcapsules are formed. Cooler quenching liquid temperatures generate spherical microcapsules, and yet cooler temperatures generate ellipsoidal-shaped microcapsules and "splatter" shaped microcapsules. The size and shape of the orifice will also have an effect on the size and shape of the resulting microcapsules. The present encapsulation technique may be carried out in conventional equipment on a small or large scale. There is no need to utilize a large spray tower or other unique manufacturing apparatus, unless highly specialized microcapsules are desired.

The microcapsules are prepared by injection of the encapsulation composition into the quenching liquid as an intact stream. Once the stream of encapsulation composition is immersed in the quenching liquid, the stream breaks up into discrete droplets that are in turn solidified to form microcapsules. The injection port for the encapsulation composition may optionally be outside the quenching liquid, or within the quenching liquid. The injection port itself is optionally heated or cooled separately to provide good temperature control.

Optionally, rather than providing separate mixing vessels for preparation of the encapsulation composition, the encapsulation composition may be formulated in line with an extruder. In such a process, the extruder is fed with pellets of the solid matrix-forming material, and the active component is added to these pellets at an appropriate point in the extrusion process. The extrusion process provides uniform distribution of the active component throughout the molten solid matrix-forming material, and provides excellent control of pressure and temperature of the encapsulation composition before injection into the quenching liquid.

The active component to be encapsulated may be any component that would benefit from controlled delivery or protection from premature reaction or adverse environmental effects. The active component may be water soluble or water insoluble. Examples of active components include vitamins, such as Vitamin C crystals and Vitamin A, β-carotene, dipeptides, such as aspartame crystals, antimicrobials and surfactants, such as didodecyldimethylammonium bromide, skin penetration enhancers such as glyceryl monolaurate, light or heavy pigments, baking powder, grinding aids for abrasives (i.e., material that interacts chemically, cools, enhances friction, or otherwise acts to assist in stock removal or enhance the lifetime of the grinding tool) such as trichloroacetic acid and trifluoroacetic acid, flavors, fragrances, enzymes, moisturizers, sunblocks/sunscreens or UV-absorbers, oxidizing agents, reducing agents, fertilizers, biocides, insect repellents, magnetic oxides (for steering particles for drug delivery), bases such as sodium hydroxide, acids such as percarboxylic acids, peroxides, persulfates, sodium hypochlorite, percarboxylic acid amides, wrinkle treatments such as alpha hydroxy carboxylic acids and especially glycolic acid, natural and synthetic lipids, catalysts such as sulfonic acid, thiols (including polythiols) 2-methyl-4-ethyl imidazole, penterythritol, Lewis acids, and Lewis acid-derived Bronsted acids such as $BF_3$, $SnCl_4$, $SbCl_5$, $SbF_5$, $PF_5$, $HBF_4$, $HPF_6$ and $HSbF_6$; platinum complexes, Raney nickel, Jeffamine™ amines (Texaco), potassium lactate, plasticizers and tackifiers, dyes, pigments, pharmaceuticals, phosphorescent materials, radioactive markers and the like.

An optional component to be incorporated as the active component may be a gas, which is condensed into liquid, dispersed under pressure (below the triple-point) in the softened solid matrix-forming material and injected into very cold quenching liquid, such as Fluorinert™ material. Fluorinert™ materials are preferred because they can remain in liquid form at very cold temperatures, thereby allowing freezing of an already cold encapsulation composition.

The solid matrix-forming materials used in the present invention are materials that are chemically inert to the active material and which can be thermally softened to a pumpable viscosity so that it can be injected as an intact stream into a quenching liquid. The solid matrix-forming material must be pumpable at a temperature below the temperature of decomposition of the active component.

Preferred solid matrix-forming materials include various thermoplastic materials, such as natural or synthetic fatty alcohols, fatty acids, fatty esters and waxes. Natural waxes include the vegetable waxes such as carnauba, cauassu, candelilla, raffia, palm, esparto, sugar cane and cotton waxes; animal waxes such as beeswax, ghedda, chinese insect, shellac, spermaceti and lanolin waxes; and mineral wax such as paraffin, microcrystalline, ozokerite, montan and syncera waxes. Synthetic and modified waxes useful as solid matrix-forming materials include the Carbowaxes, Abril waxes, Armid and Armowaxes (Armour & Co.) and Chlorax chlorinated paraffin wax (Watford Chemical Co.). It will be appreciated that waxes are a mixture of various components, and that each type of wax is itself available in a number of different grades.

Other thermoplastic materials are useful as solid matrix-forming materials, including polyethylenes such as Polywax™ from Petrolite, Inc., polypropylenes, polyesters, polyvinyl chlorides, tristarch acetates, polyethylene oxides, polypropylene oxides, polyvinylidene chloride or fluoride, polyvinyl alcohols, polyvinyl acetates, polyacrylates, polymethacrylates, vinyl functional polymers, urethanes, polycarbonates and polylactones.

Preferred Solid matrix-forming materials for use with Vitamin C or other water-soluble components include carnuba wax, yellow beeswax, white beeswax, paraffin and linear or branched polyethylenes.

The solid matrix forming material may optionally comprise blends of waxes or waxes having an additional additive that will help to seal the ultimate particle. Examples of such additives for waxes include chicle-type resins. The use of such additives avoid cracking by inhibiting the crystallization of the wax over the relevant temperature drop while cooling. Such additives affect the volumetric coefficient of fusion, thereby reducing the overall volumetric change when the particle solidifies.

An example of an additive to be incorporated into certain waxes in particular, for example carnauba wax, is polyethylene. While not being limited by theory, it is believed that such polymer additives act as a bridge or web to reinforce the particle as it cools. Preferably additives are provided to the solid matrix-forming material in up to 5% of the solid matrix-forming material.

The solid matrix-forming material may optionally be provided with an additional filler component. Such a filler could reduce the cost of the matrix or modify the diffusion of the active component within the microcapsule. For example, platelet shaped filler materials would provide additional resistance to escape of active component from the microcapsule by requiring the active component to travel a tortuous pathway in the diffusion process. Examples of filler materials include mica, barium ferrite, silica., graphite and powdered carbon.

The microcapsule as formed in the present invention may be rendered porous by incorporating a volatile component in the solid matrix-forming material. During or immediately after injection into the quenching liquid, the volatile component will tend to escape from the microcapsule before complete solidification thereof, thus providing a porous network in the microcapsule.

The quenching liquid is any fluid or blend of fluids that is substantially non-reactive with the active component and the solid matrix-forming material, and is a poor solvent for the solid matrix-forming material. Preferably, the quenching liquid is a poor solvent for both the active component and the solid matrix-forming material. Preferably, the quenching liquid should have lower surface energy and relatively weak intermolecular forces in order to facilitate breakup of the intact stream of encapsulation composition into microcapsules.

It is preferred that the quenching liquid have a comparatively low thermoconductivity. If the thermoconductivity is too high, energy will be rapidly removed from the droplets of the molten encapsulation composition which in turn rapidly freezes the encapsulation composition into contoured shapes, such as teardrops, before allowing surface tension to form a round droplet. As a general rule, lower viscosity quenching liquids generate smaller particles. This effect however, can be modified by adjustment in velocity of the stream of encapsulation composition into the quenching liquid and by modification of the viscosity or the temperature of the encapsulation composition.

Examples of quenching liquids include any of the various oils such as palm oil, neetfoot oil, rapeseed oil, peanut oil, tung oil, coconut oil, jojoba oil petroleum oils, synthetic oils. Other less viscous fluids, such as hydrocarbons, water etc., may also be considered to be viable options under certain conditions. Such quenching liquids may be reactive or good solvents for a number of potential active components or solid matrix-forming materials. Selection of the more reactive, and potentially less expensive, quenching liquid requires careful matching of ingredients following the teachings provided herein.

The quenching liquid may optionally be modified so the active component is not soluble therein by saturating the quenching liquid with the active component. Such saturation would render the active component that is provided in the encapsulation composition insoluble in the thus modified quenching liquid. Because this modification may result in unwanted addition of active component deposits downstream on the outside of the microcapsule as the encapsulation composition cools and solidifies, this modification is not generally preferred. In addition to providing a potentially unpredictable dosage of active component, there may be a problem with morphology being different in the deposit of active component formed on the outside of the microcapsule as opposed to that encapsulated within the microcapsule.

Preferred quenching liquids are those that are substantially inert to most substances. Such generally inert fluids include:

(I) A fluid silicone compound having the structure (II) The compound of I in which 25% of the —$CH_3$ substituents are replaced by phenyl groups.

(III) The compound of I in which 100% of the —$CH_3$ substituents are replaced by phenyl groups.

(IV) Tributyl amine $(C_4H_9)_3N$, and isomers thereof, in which the hydrogen has been replaced by fluorine.

(V) A mixture of perfluoro cyclic ether isomers $(C_8F_{16}O)$

Particularly preferred quenching liquids are the straight, branched and cyclic perfluorinated hydrocarbons, perfluorinated ethers and amines such as Fluorinert™ compounds commercially available from 3M. Particularly preferred quenching liquids are the straight chain perfluorinated hydrocarbons.

In another aspect of the present invention, additional components that are to be incorporated in the microcapsule at the outer surface of the microcapsule may be dispersed or dissolved in the quenching liquid. Depending on the solubility characteristics of these additional components, the components will adhere to the outer surface of the microcapsule or will migrate into the outer surface of the microcapsule. Components that may be so incorporated include abherents, additional active components that are the same or different from the active component that is encapsulated within the solid matrix-forming material, a color-imparting material such as a dye or pigment, magnetic particles, energy absorbing particles, diffusion modification particles and the like. These components optionally may contain reactive functionalities that chemically react with functionalities provided on the solid matrix-forming material.

Abherents are substances that prevent or reduce adhesion of a material to itself or other materials, and provide particular benefit to the microcapsules of the present invention. One category of abherent, the anti-blocking agents or flow aids, are particularly beneficial components of the present invention. For purposes of this invention, anti-blocking agents or flow aids may defined as small particles that themselves are not tacky but which adhere to the surface or may embed themselves into the surface of the microcapsule. Preferably, the anti-blocking agents are less than one tenth of the diameter of the microcapsule and more preferably less than one one-hundredth of the diameter of the microcapsule. The anti-blocking agent is provided as a suspension in the quenching liquid and may be of a hydrophobic or a hydrophilic nature. Usually, the hydrophobicity is preferred to be similar to the general nature of the particle to which it is to be attached.

Examples of anti-blocking agents include talc, calcium stearate, Volan™ anti-blocking agent, dry lubricants such as graphite, and Cab-o-sil™ silicon dioxide (Cabot Corp., Tuscola Ill.). A preferred silicon dioxide is Cab-o-sil™ TS 720, which is an easy-to-disperse hydrophobic particle. An additional bridging agent or anti-blocking agent is Cab-o-sil™ M-5. This particular silicon dioxide may require a great deal of energy to disperse in Fluorinert™ compositions, but provides a fairly stable colloidal suspension that may be easily handled.

Alternatively, the anti-blocking agent may be a surfactant that associates with the outer surface of the encapsulated material, providing a low energy surface that discourages blocking.

A color imparting material may optionally be provided either in the encapsulation composition or a quenching liquid. A color-imparting material may be selected from a pigment or dye or other means to impart color. The preferred dyes for use in the composition of the present invention are dyes that are approved for drug and cosmetic use (D&C) or food, drug and cosmetic use (FD&C dyes). Such dyes are well-known commercially available materials, with a chemical structure being described, e.g. in 21 C.F.R. §74 and the *CTFA Cosmetic Ingredient Handbook,* 1988, published by the Cosmetics, Toiletry, Fragrance Association, Inc. Dyes are most preferably colorfast, i.e. non-leaching and non-bleaching.

When the quenching liquid selected is Fluorinert™ or another highly inert liquid, co-solvents or other solvation assisting components may be required to provide a uniform solution of a dye or other component to be incorporated on the surface of the microcapsule. An example of a co-solvent that may be useful for incorporating dye in Fluorinert™ is xylenehexafluoride. Optional components such as radioactive markers and phosphorescent materials may also be incorporated in or on the surface of the microcapsule. The dye could optionally be provided in a very thin distribution on the outer shell of the encapsulated particle. Small amounts of dye incorporation are preferred because of lower risk of contamination of the active component with the dye material. Additionally, the same or better perception of color may be achieved with a reduced amount of dye.

Microcapsules according to the present invention may optionally be provided with multiple coatings of different solid matrix-forming material through sequential coating steps or multiple applications of additional components to the outside of the microcapsule by softening the solid matrix-forming material and injecting into a second quenching liquid. This provides flexibility in both assuring complete coating and optionally multiple-step triggering mechanisms.

The microcapsule as presently prepared may additionally be provided with functionalities that may be further cross-linked or otherwise reacted to harden or tighten the encapsulation shell.

Before the thermally softened solid matrix-forming material is placed in a pressurized container and pumped through a die, it is preferred to hot-filter the material to avoid plugging of the die with impurities or incompletely dissolved material. Additional mixing elements may be provided along the processing path, including ultrasonic mixing devices.

Size or coating thickness of the microcapsule may be varied by varying the pressure or stream velocity of the encapsulation composition, the orifice size and geometry, the viscosity of the encapsulation composition or the viscosity of the quenching liquid.

The present microcapsules optionally may be of a shape that is substantially the same as the shape of an underlying solid active component, depending on the coating thickness of the solid matrix around the solid active component. Thus, if a small coating-to-solid active component mass ratio is selected, the shape will generally conform to the shape of the underlying solid active component. When a higher coating-to-solid active component weight ratio is provided, the microcapsule may tend to be more spherical in shape.

Trichloroacetic acid is useful as an aid in grinding operations, but cannot generally be incorporated into a coated abrasive sheet without adversely affecting the phenolic resin used to bind the abrasive to the sheet during the manufacturing process. Trichloroacetic acid may, however, be added to the surface of the sheet without adverse effect by utilizing the present invention. The acid may be encapsulated in a solid matrix having a melting temperature above the cure temperature of the phenolic resin.

As one option, the trichloroacetic acid may be quenched using Fluorinert™ material, and any acid residing on the surface of the capsule washed off by a separate water rinse. Alternatively, the acid may be quenched in a water bath. Acid contained within the matrix remains and is not washed way by the water due to the short time period between injection into the quenching liquid and surface solidification of the matrix. Acid residing at the surface of the capsule is immediately washed away by the water bath.

DETAILED DESCRIPTION OF DRAWINGS

Figure 1:
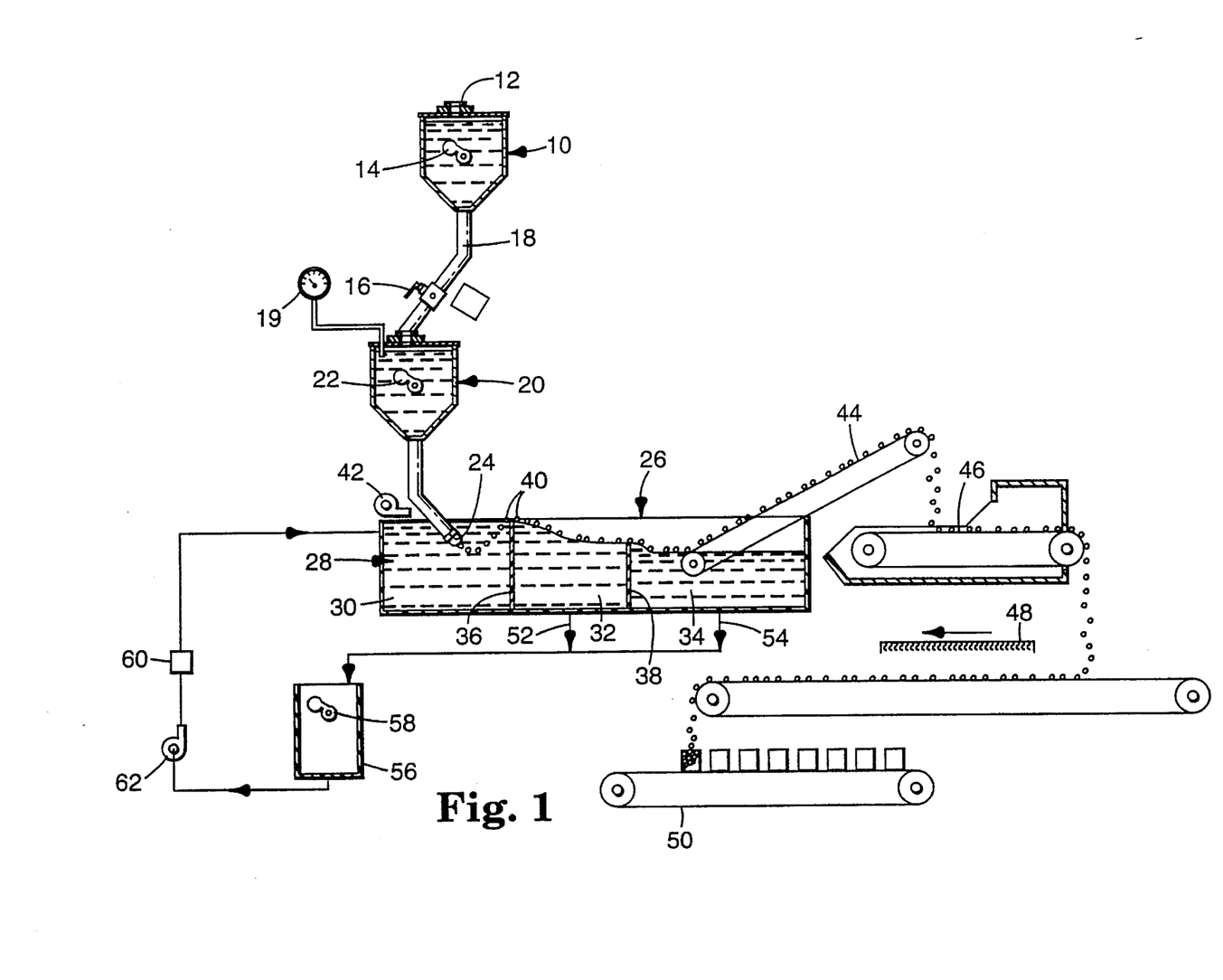
FIG. 1 is a side view of an apparatus for carrying out the method of encapsulating active components as disclosed herein.

FIG. 1 is a device for encapsulating active ingredients according to the present invention. Molten solid matrix-forming material is introduced into mixing vessel 10 through feeding port 12 and kept at a controlled temperature. The active component is dispersed in the solid matrix-forming molten material with the assistance of the stirring device 14. Valve 16 may be opened, thereby allowing material to traverse through temperature controlled conducting pipe 18 to pressurized vessel 20. Pressurized vessel 20 may be held at controlled temperature and pressure to allow for controlled injection of the molten encapsulation composition. Even dispersion of the active component through the molten solid matrix-forming material is maintained with the assistance of stirring device 22. Encapsulation composition is injected from pressurized vessel 20 through injection nozzle 24 into solidification tank 26. Solidification tank 26 contains quenching liquid 28, which is also held at controlled temperatures. Preferably, solidification tank 26 contains three separate temperature control zones comprising congealing zone 30, solidification zone 32, and collection zone 34. These zones are preferably segregated one from another by weir 36 and weir 38. Quenching liquid 28 located in congealing zone 30 is maintained at a temperature below the melting temperature of encapsulation composition, so that as the intact stream of encapsulation composition is expressed from injection nozzle 24, discrete congealed microcapsules 40 are formed. As the congealed microcapsules 40 rise to the surface of quenching liquid 28, they are blown across the surface of quenching liquid 28 by blower 42 over weir 36, so that they enter solidification zone 32. Solidification zone 32 is maintained at a yet lower temperature to further solidify the microcapsule. Microcapsules 40 continue to traverse over weir 38 to collection zone 34, where they are taken up by belt 44 or other appropriate collection means and cycled through optional washing and screening apparatus 46 to dryer 48. The microcapsules may be packaged at packaging apparatus 50. Quenching liquid 28 may be recycled by removing from solidification tank 26 through exit ports 52 and 54 and introducing into quenching liquid conditioning vessel 56. Optional additional components may be added to quenching liquid conditioning vessel 56 and dispersed with the assistance of stirring device 58. The temperature of quenching liquid 28 may be controlled by heat exchange 60 and supplemental heating or cooling elements in solidification zone 32 and collection zone 34. Quenching liquid 28 may be reintroduced to solidification vessel 26 using pump 62.

Figure 2:
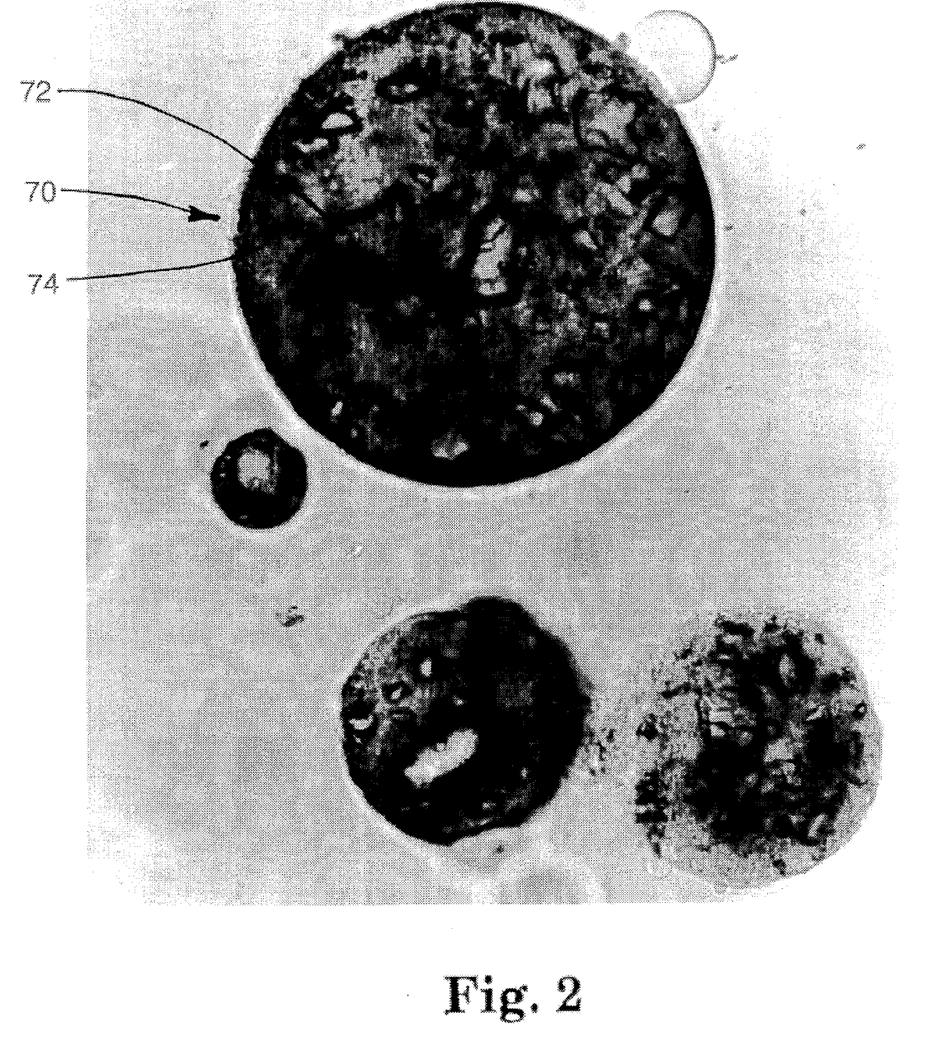
FIG. 2 is a photomicrograph of a cross-sectional view of microcapsules made according to the present invention.

FIG. 2 is a photomicrograph of a microcapsule made in accordance with the present invention. The FIG. shows the cross-sectional view of microcapsule 70 having crystal active component 72 encapsulated by solid matrix-forming material 74.

Figure 3:
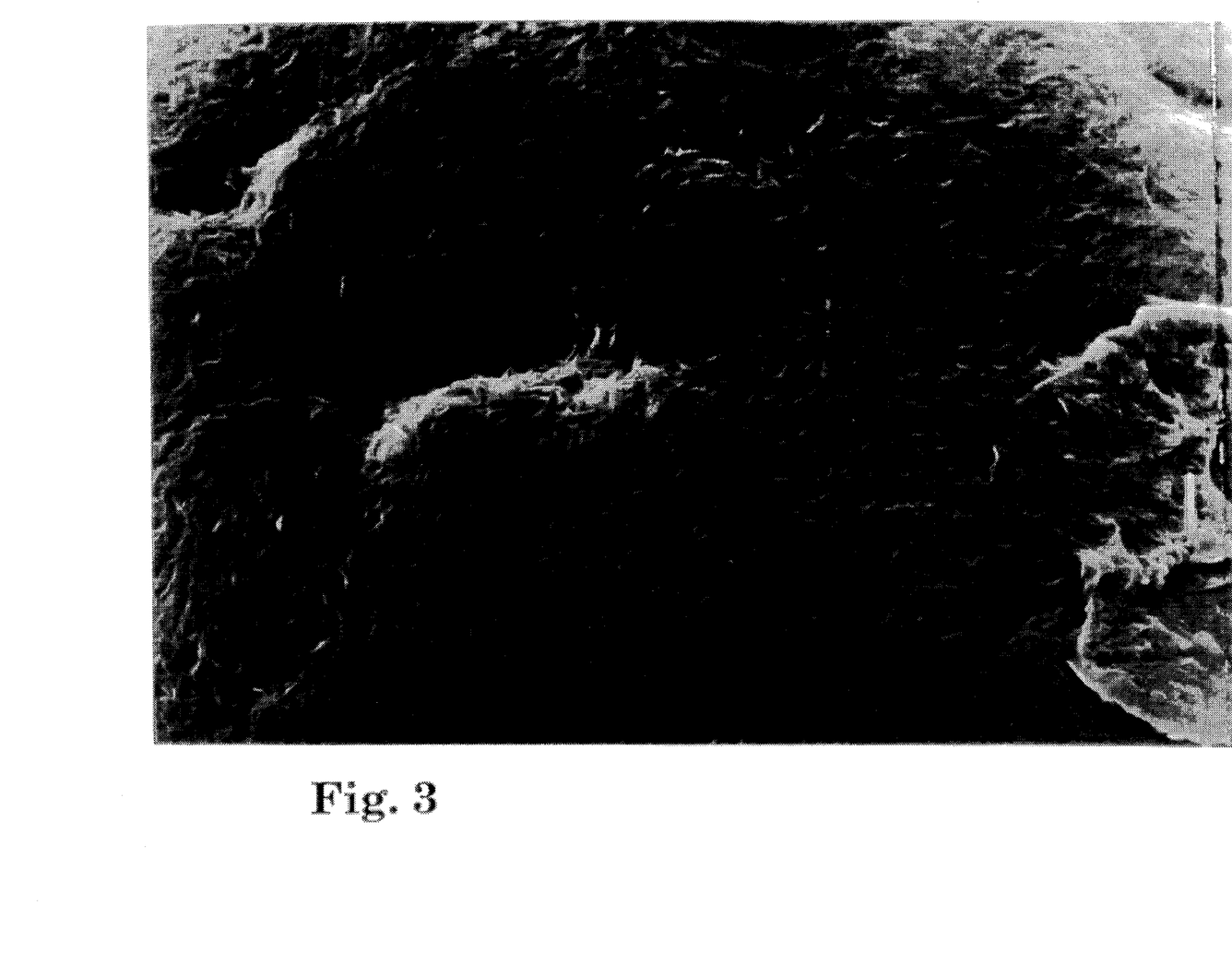
FIG. 3 is a photomicrograph of the surface of a microcapsule made in accordance with the present invention.

FIG. 3 is a photomicrograph of a microcapsule made in accordance with the present invention, wherein the photomicrograph is of a much higher magnification so that the surface of the microcapsule may be more closely examined and with more detail.

Figure 4:
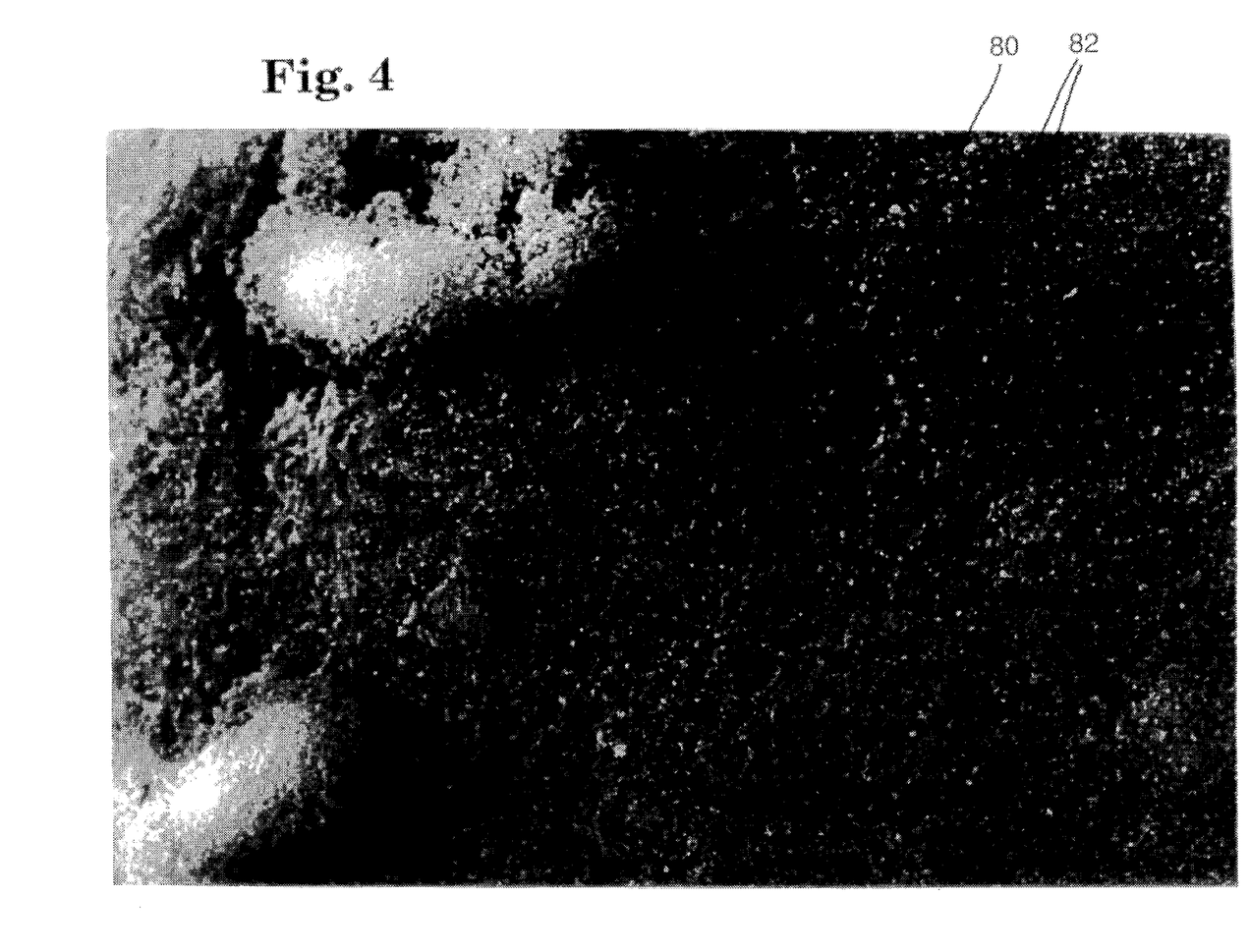
FIG. 4 is a photomicrograph of the surface of a microcapsule having anti-blocking agents made in accordance with the present invention.

FIG. 4 is a photomicrograph of a microcapsule made in accordance with the present invention at the same degree of magnification as the micrograph shown in FIG. 3. In this micrograph, microcapsule surface 80 is apparent. Anti-blocking particles 82 are adhered to surface 80 of the microcapsule, thereby providing protection against agglomeration or blocking of the microcapsules.

The microcapsules of the present invention can provide superior controlled release, because microcapsules can be made with uniform and small size. A small core is particularly preferred when immediate release by enzymes such as those contained in the stomach is desired. The present microcapsules may be preferred in certain applications over traditional "hard-shell" microcapsules that release their active component by breaking such as would be caused by mastication. Particles encapsulated in wax do not necessarily release when masticated because there may still be integrity of the coating immediately adjacent to the active component.

An alternative construction for manufacturing the present microcapsules comprises a column having encapsulation composition injected therein. If the encapsulation composition is less dense than the quenching liquid, the composition would be injected into the bottom of the column. Microcapsules formed in this process would float to the top of the column, possibly through a temperature gradient in the column. Similarly, encapsulation compositions that are more dense than the quenching fluid could be injected at the top of the column, with microcapsules sinking to the bottom of the column.

A number of means may be used to trigger release of the material from the microcapsules described herein. Included in such release mechanisms are, heat, pH, solvents or physical crushing of the capsule.

An example of a solvent release system is the incorporation of a solvent for the solid-matrix forming material in a separate capsule such as a polyoxymethylene urea capsule. In use, the capsules are combined together in a single formulation and may be applied, for example, to the skin. Rubbing of this formulation with, for example, a finger, ruptures the polyoxymethylene urea capsule and releases the solvent. The solvent, in turn, solvates the solid matrix-forming material thereby releasing the active component. An example of such a solvent is Finsolv™TN, which is safe and non-drying for use on the skin. The Finsolv™ TN solvent serves to solubilize the wax that is the solid matrix for the microcapsule, thereby making the active ingredient available directly to the skin. A particularly preferred solid matrix-forming material in this release mechanism is Finsolv® 116 fatty benzoate esters, which is particularly soluble in Finsolv™ TN solvent.

An additional alternative release mechanism is incorporation of energy absorbing particles in or on the solid matrix of the microcapsule. When energy is applied to the particle, the energy absorbers on or in the solid matrix direct the heat in aid of melting of the solid matrix, thereby releasing the active component.

The following examples are provided for illustrative purposes, and are not intended to be limiting of the scope of the present invention.

EXAMPLE 1

Carnauba wax/Vitamin C Microcapsules

Seventy-three grams of ultra-fine powder (<10μm) Vitamin C (Hoffmann-LaRoche Inc., Nutley N.J.) were dispersed in hot melt 150 grams of carnauba wax (Aldrich Chemical Co., Milwaukee, Wis.) with 7.5 grams of polyethylene homopolymer grade 7A (Allied Corporation A-C® polyethylenes, Morristown, N.J.) at 120° C., and agitated by a 4-bladed turbine stirrer (800 rpm, 6 cm dia.). The system was agitated for 10 min. to form an dispersion. The solution was transferred to a 105° C. preheated reactor equipped with a 6-bladed turbine stirrer (200 rpm, 3.5 cm dia.). The thus prepared encapsulation composition was injected by pressurizing the reactor. The stream of encapsulation composition was received into a deep beaker containing FC-77 perfluorocarbon fluid (3M, St. Paul, Minn.) at 60° C. The microcapsules were recovered by filtering and air-drying.

EXAMPLE 2

Cab-O-Sil® coated Vitamin C Microcapsules

The procedure of Example 1 was repeated except 2 grams of Cab-O-Sil® TS-720 (Cabot Corporation, Tuscola, Ill.) were dispersed in the FC-77 perfluorocarbon fluid.

EXAMPLE 3

Victoria Blue BO coated Microcapsules

The procedure of Example 2 was repeated except one gram of Victoria Blue BO crystal (Du Pont De Nemours & Co., Wilmington, Del.) was dissolved in 40 ml of 1,3-Bis(trifluoromethyl)benzene (Aldrich Chemical Co., Milwaukee, Wis.), then mixed in the FC-77 fluid.

EXAMPLE 4

Polywax® 500/Vitamin C Microcapsules

Microcapsules were prepared as in Example 1, except using the following materials and reaction conditions:

Vitamin C 45 grams
Polywax® 500 150 grams
Cab-O-Sil® TS-720 0.5 grams
Brij® 72 (ICI Americas Inc., Wilmington Del.) 3 grams
Pre-mixing temperature 120° C.
Reactor temperature 105° C.
FC-77 fluid 800 ml at 60° C.

EXAMPLE 5

Carnauba wax/NutraSweet™ Microcapsules
Microcapsules were prepared as in Example 1, except using the following materials and reaction conditions:
  NutraSweet™ (NutraSweet Co., Ill.) 30 grams
  Carnauba wax 150 grams
  Pre-mixing temperature 104° C.
  Reactor temperature 104° C.
  FC-77 fluid 800 ml at 60° C.

EXAMPLE 6

Beeswax/Vitamin C Microcapsules
Microcapsules were prepared as in Example 1, except using the following materials and reaction conditions:
  Vitamin C 74 grams
  Beeswax (Aldrich Chemical Co., Milwaukee, Wis.) 150 grams Pre-mixing temperature 101° C.
  Reactor temperature 91° C.
  FC-77 fluid 800 ml/Cab-O-Sil® TS-720 1.5 grams at 50° C.

EXAMPLE 7

Beeswax/Beta carotene (30% in Vegetable oil) Microcapsules
Microcapsules were prepared as in Example 1, except using the following materials and reaction conditions:
  Beta Carotene (30% in vegetable oil )(Hoffmann-LaRoche Inc., Nutley, N.J.) 21 grams
  Corn starch (Argo® Corn Starch Dept., Coventry, Conn.) 16.5 grams
  Beeswax (Aldrich Chemical Co., Milwaukee, Wis.) 150 grams
  Pre-mixing temperature 88° C.
  Reactor temperature 88° C.
  FC-77 fluid 800 ml/Cab-O-Sil® TS-720 1.5 grams at 47° C.

EXAMPLE 8

Finsolv® 116/Vitamin C Microcapsules
Microcapsules were prepared as in Example 1, except using the following materials and reaction conditions:
  Vitamin C 74 grams
  Finsolv® 116 (Finetex Inc., Elmwood Park, N.J.) 150 grams
  Pre-mixing temperature 76° C.
  Reactor temperature 52° C.
  FC-77 fluid 800 ml/Cab-O-Sil® TS-720 1.5 grams at 15° C.

EXAMPLE 9

Finsolv® 116/Glyceryl monolaurate
Microcapsules were prepared as in Example 1, except using the following materials and reaction conditions:
  Glyceryl monolaurate 5 grams
  Finsolv® 116 85 grams
  Pre-mixing temperature 76° C.
  Reactor temperature 52° C.
  FC-77 fluid 800 ml/Cab-O-Sil® TS-720 1.5 grams at 15° C.

EXAMPLE 10

Finsolv® 116/Didodecyldimethylammonium bromide Microcapsules
Microcapsules were prepared as in Example 1, except using the following materials and reaction conditions:
  Didodecyldimethylammonium bromide 75 grams
  Finsolv® 116 150 grams
  Pre-mixing temperature 76° C.
  Reactor temperature 52° C.
  FC-77 fluid 800 ml/Cab-O-Sil® TS-720 1.5 grams at 11° C.

EXAMPLE 11

Paraffin P-116/Vitamin C Microcapsules
Microcapsules were prepared as in Example 1, except using the following materials and reaction conditions:
  Vitamin C 74 grams
  Paraffin wax P-116 (Sun Oil Co.) 150 grams
  Brij® 72 3 grams
  Pre-mixing temperature 84° C.
  Reactor temperature 72° C.
  FC-77 fluid 800 ml/Cab-O-Sil® TS-720 1.5 grams at 39° C.

EXAMPLE 12

Paraffin blend/baking powder Microcapsules
Microcapsules were prepared as in Example 1, except using the following materials and reaction conditions:
  Calumet® baking powder (Kraft General Foods, Inc., White Plains, N.Y.) 73 grams
  Paraffin wax P-116 110 grams
  Vybar 260 85 grams
  Pre-mixing temperature 83° C.
  Reactor temperature 83° C.
  FC-77 fluid 800 ml/Cab-O-Sil® TS-720 1.5 grams at 38° C.

EXAMPLE 13

Tetradecanol/Vitamin C Microcapsules
Microcapsules were prepared as in Example 1, except using the following materials and reaction conditions:
  Vitamin C 74 grams
  Tetradecanol 150 grams
  Pre-mixing temperature 76° C.
  Reactor temperature 58° C.
  FC-77 fluid 800 ml/Cab-O-Sil® TS-720 1.5 grams at 27° C.

EXAMPLE 14

(23 wt % Washable blend/77 wt % paraffin-stearic acid) crayon base/Zns:Cu phosphor Microcapsules were prepared as in Example 1, except using the following materials and reaction conditions:

Phosphorescent pigment 6SSUY (United Mineral &

Chemical Corp., N.J.) 123 grams Paraffin/stearic blend 94 grams

Washable blend crayon base (Binney & Smith Inc., Easton, Pa.) 28 grams

Premixing temperature 83° C.

Reactor temperature 83° C.

FC-77 fluid 800 ml/Cab-O-Sil® TS-720 1.0 grams at 43° C.

EXAMPLE 15

Polywax® 500/Trichloracetic acid Microspheres

Microcapsules were prepared as in Example 1, except using the following materials and reaction conditions:

Trichloroacetic acid 75 grams

Polywax® 500 polyethylene (Petrolite Corporation Polymers Division, Tulsa, Okla.) 150 grams Premixing temperature 120° C.

Reactor temperature 105° C.

FC-43 fluid (3M Co., St. Paul, Minn.) 400 ml at 40° C.

EXAMPLE 16

Carnauba wax/chicle (NOVA base T) Vitamin C Microspheres

Microcapsules were prepared as in Example 1, except using the following materials and reaction conditions:

Vitamin C 74 grams

Carnauba wax 150 grams

Chicle (NOVA base T) (L. A. Dreysuss Co., South Plainfield, N.J.)

10 grams

Premixing temperature 112° C.

Reactor temperature 104° C.

FC-77 fluid 800 ml/Cab-O-Sil® TS-720 2.8 grams at 61° C.

Measurement of Encapsulated Vitamin C by Differential Scanning Calorimetry

Pure Vitamin C crystals were measured as a control. The endotherm peak of Vitamin C was 194° C. and 258.7 Joules per gram Vitamin C as measured by differential scanning calorimetry. A suitable amount of preweighed Vitamin C microcapsules was placed in the DSC-Cell and analyzed with a DU PONT 2000 Differential Scanning Calorimeter. The temperature range was from 5° C. to 250° C., heating rate was chosen to be 10° C. per minute. Samples of Examples 1, 2, 3, 4, 6, 8, 11, and 13 were measured and the amount of Vitamin C present in the microcapsules was calculated. This value was converted into equivalent weight percentages of whole microcapsules and were all found to be about 30 wt %, which is same as the ratio of reactants charged to the encapsulation composition.

This experiment shows that substantially all of the Vitamin C charged into the encapsulation composition is encapsulated in the microcapsules without degradation or loss.

Release study of Vitamin C microcapsules

Two grams of Vitamin C-containing microcapsules (of Example 1) were soaked in 150 ml of distilled deionized water containing a trace amount of Tween 80 at 24° C. Samples were withdrawn at different times, washed with water, vacuum dried and examined by Differential Scanning Calorimetry to determine their Vitamin C content. The microcapsules were found to initially comprise 30% by weight of Vitamin C. After 40 days, the microcapsules were found to comprise 10% by weight of Vitamin C. This is excellent Vitamin C retention as compared to conventional ethyl cellulose coated Vitamin C systems, which are completely depleted of Vitamin C after eight hours under the same conditions.

Examination of the Structure of the Microcapsules

The degree of dispersion of Vitamin C crystals in the microcapsules was examined by using Backscattered Electron Imaging (BSEI) which is generally more affected by compositional differences than Secondary Electron Imaging (SEI). This technique allows the crystal morphology and the matrix surrounding the crystal to be examined. The structure of microcapsules may also be examined by Transmitted Differential Interference Contrast (TDIC) microscopy. A small quantity of NutraSweet/carnauba wax microcapsules (Example 5) and Vitamin C/carnauba wax microcapsules (Example 1)to be examined was combined with 3M Scotchcast #8 electrical casting resin in two separate compositions, placed in molds, and allowed to cure overnight. The cured mounts were then microtomed with an LKB Histo Range to produce approximately 25 micron thick sections through the microcapsules. The prepared sections were immersed in a mounting oil (ND=1.515) on a glass slides, and then examined by Transmitted Differential Interference Contrast (TDIC) microscopy. Microcapsules prepared by the methods of this invention have discrete cores which retain their morphology and which are dispersed randomly throughout the microcapsules.

We claim:

1. A process for encapsulating an active component comprising:

a) preparing an encapsulation composition by dispersing or dissolving said active component in a solid matrix-forming material that has been thermally softened to at least a pumpable state, b) preparing a bath of a quenching liquid, said quenching liquid being substantially non-reactive with the active component and the solid matrix-forming material, and said quenching liquid being a poor solvent for the active component and the solid matrix-forming material, wherein at least a portion of said bath is at a temperature below the solidification temperature of said solid matrix-forming material, c) injecting said encapsulation composition as an intact stream into said quenching liquid, and d) allowing said encapsulation composition to break up into droplets and solidify in said quenching liquid to form microcapsules; wherein said solid matrix-forming material is selected from the group consisting of natural fatty alcohols, synthetic fatty alcohols, natural fatty acids, synthetic fatty acids, natural fatty esters, synthetic fatty esters, natural waxes, synthetic waxes, polyethylenes, polypropylenes, polyesters, polyvinyl chlorides, tristarch acetates, polyethylene oxides, polypropylene oxides, polyvinylidene chloride, polyvinylidene fluoride, polyvinyl alcohols, polyvinyl acetates, polyacrylates, polymethacrylates, vinyl functional polymers, urethanes, polycarbonates, polylactones and mixtures thereof.

2. The process of claim 1, wherein an additional component to be incorporated at the outer surface of the microcapsule is dispersed or dissolved in the quenching liquid.

3. The process of claim 2, further comprising the steps of e) heating said microcapsules to soften the solid matrix-forming material, and f) placing said microcapsules into a second quenching liquid having an additional component to be incorporated at the outer surface of the microcapsule dispersed or dissolved therein.

4. The process of claim 1, wherein said quenching liquid has an anti-blocking material dispersed or dissolved therein.

5. The process of claim 1, wherein said quenching liquid has a color-imparting material dispersed or dissolved therein.

6. The process of claim 5, wherein said color-imparting material is a dye.

7. The process of claim 1, wherein said active component is water-soluble.

8. The process of claim 7, wherein said active component is Vitamin C.

9. The process of claim 7, wherein said active component is aspartamine.

10. The process of claim 1, wherein said active component is a grinding aid.

11. The process of claim 1, wherein said active component is a catalyst.

12. The process of claim 1, wherein said solid matrix-forming material additionally comprises a diffusion-modifying filler.

13. The process of claim 1, wherein said quenching liquid comprises a perfluorocarbon.

14. A process for encapsulating an active component comprising:

a) preparing an encapsulation composition by dispersing or dissolving said active component in a solid matrix-forming material that has been thermally softened to at least a pumpable state, b) preparing a bath of a quenching liquid, said quenching liquid being substantially non-reactive with the active component and the solid matrix-forming material, and said quenching liquid being a poor solvent for the solid matrix-forming material, wherein at least a portion of said bath is at a temperature below the solidification temperature of said solid matrix-forming material, c) injecting said encapsulation composition as an intact stream into said quenching liquid, and d) allowing said encapsulation composition to break up into droplets and solidify in said quenching liquid to form microcapsules, wherein said solid matrix-forming material is a polyethylene.

15. A process for encapsulating an active component comprising:

a) preparing an encapsulating composition by dispersing or dissolving said active component in a solid matrix-forming material that has been thermally softened to at least a pumpable state, b) preparing a bath of a quenching liquid, said quenching liquid being substantially non-reactive with the active component and the solid matrix-forming material, and said quenching liquid being a poor solvent for the solid matrix-forming material, wherein at lest a portion of said bath is at a temperature below the solidification temperature of said solid matrix-forming material, c) injecting said encapsulation composition as an intact stream into said quenching liquid, and d) allowing said encapsulation composition to break up into droplets and solidify in said quenching liquid to form microcapsules wherein said solid matrix-forming material is beeswax.

16. A process for encapsulating an active component comprising:

a) preparing an encapsulation composition by dispersing or dissolving said active component in a solid matrix-forming material that has been thermally softened to at least a pumpable state, b) preparing a bath of a quenching liquid said quenching liquid being substantially non-reactive with the active component and the solid matrix-forming material, and said quenching liquid being a poor solvent for the solid matrix-forming material, wherein at least a portion of said bath is at a temperature below the solidification temperature of said solid matrix-forming material, c) injecting said encapsulation composition as an intact stream into said quenching liquid, and d) allowing said encapsulation composition to break up into droplets and solidify in said quenching liquid to form microcapsules, wherein said solid matrix-forming material is canauba wax.

17. A system for delivery of an active component comprising i) a microcapsule made according to a process for encapsulating an active component comprising:

a) preparing an encapsulation composition by dispersing or dissolving said active component in a solid matrix-forming material that has been thermally softened to at least a pumpable state, b) preparing a bath of a quenching liquid, said quenching liquid being substantially non-reactive with the active component and the solid matrix-forming material, and said quenching liquid being a poor solvent for the solid matrix-forming material, wherein at least a portion of said bath is at a temperature below the solidification temperature of said solid matrix-forming material, c) injecting said encapsulation composition as an intact stream into said quenching liquid, and d) allowing said encapsulation composition to break up into droplets and solidify in said quenching liquid to form microcapsules; and ii) microcapsules having a liquid capsule fill, wherein the liquid capsule fill is a solvent for the solid matrix-forming material of Component i);

wherein said solid matrix-forming material is selected from the group consisting of natural fatty alcohols, synthetic fatty alcohols, natural fatty acids, synthetic fatty acids, natural fatty esters, synthetic fatty esters, natural waxes, synthetic waxes, polyethylenes, polypropylenes, polyesters, polyvinyl chlorides, tristarch acetates, polyethylene oxides, polypropylene oxides, polyvinylidene chloride, polyvinylidene fluoride, polyvinyl alcohols, polyvinyl acetates, polyacrylates, polymethacrylates, vinyl functional polymers, urethanes, polycarbonates, polylactones and mixtures thereof.

* * * * *